United States Patent [19]

Yale et al.

[11] 3,965,101
[45] June 22, 1976

[54] 1-(O-BROMO-PHENOXYALKYL)-1,2-DIHYDRO-2-IMINOPYRIMIDINES

[75] Inventors: Harry Louis Yale, New Brunswick, N.J.; Ramesh B. Petigara, Lansdale, Pa.

[73] Assignee: E. R. Squibb & Sons, Inc., Princeton, N.J.

[22] Filed: Mar. 7, 1975

[21] Appl. No.: 556,510

Related U.S. Application Data

[62] Division of Ser. No. 382,803, July 26, 1973, Pat. No. 3,868,374.

[52] U.S. Cl. .................. 260/256.4 H; 260/256.4 C
[51] Int. Cl.[2] ...................................... C07D 239/42
[58] Field of Search .............. 260/256.4 H, 256.4 C

[56] References Cited
OTHER PUBLICATIONS

Brown et al., *Chemical Abstracts*, vol. 50 (1956), 10730.
Goerdeler et al., *Chemical Abstracts*, vol. 58 (1963), 12557.

*Primary Examiner*—Paul M. Coughlan, Jr.
*Attorney, Agent, or Firm*—Lawrence S. Levinson; Merle J. Smith; Burton Rodney

[57] ABSTRACT

Compounds of the formula

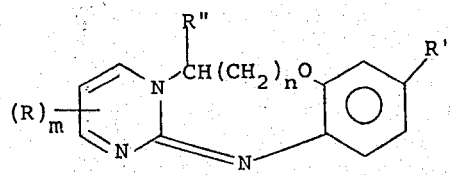

exhibit central nervous system stimulating properties and act as muscle relaxants. 6H-Pyrimido [1,2-c] [1,3,5]benzoxadiazepine is prepared from 1-(o-Benzophenoxymethyl)-1,2-dihydro-2-iminopyrimidine.

3 Claims, No Drawings

1-(O-BROMOPHENOXYALKYL)-1,2-DIHYDRO-2-IMINOPYRIMIDINES

This is a division, of application Ser. No. 382,803, filed July 26, 1973, U.S. Pat. No. 3,868,374.

OBJECTS OF THE INVENTION

It is an object of the present invention to provide new compounds having central nervous system (CNS) stimulating activity. Another object is to provide new compounds having muscle relaxant properties. A further object is to provide intermediates for the preparation of the final compounds of the invention. Yet another object is to provide a method for the preparation of both the intermediate and the final compounds of the present invention. A still further object is to provide pharmaceutical compositions containing as active ingredients the final compounds of the present invention. These and other objects of the present invention will be apparent from the following description.

SUMMARY OF THE INVENTION

The compounds of the present invention have the following formulae

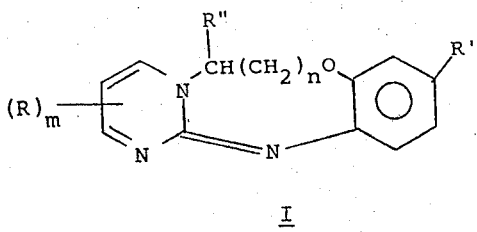

I wherein $m$ may be 1 or 2; when $m$ is 1, R occupies either position-4 or -5 of the original 2-aminopyrimidine, but when R is halogen it occupies only position-5; when $m$ is 2, the two R's occupy the 4- and 5-positions of the original 2-aminopyrimidine, but only one of the two R-substituents can be halogen and it must occupy the 5-position;

R may be the same or different and may be hydrogen, halogen (F, Cl, or Br), alkyl of from 1 to 4 carbons, benzyl, phenyl, or mono-substituted phenyl wherein the substituent may be halogen (F, Cl, Br or I), alkyl of from 1 to 4 carbons, alkoxy of from 1 to 4 carbons, or trifluoromethyl;

R' may be hydrogen, halogen (F, Cl, Br or I), alkyl of from 1 to 4 carbons, alkylsulfonyl wherein the alkyl radical has from 1 to 4 carbons, dialkylamidosulfonyl wherein each alkyl radical may have from 1 to 4 carbons, trifluoromethyl;

$n$ may be 0 or 1;

and R'' may be alkyl of from 1 to 4 carbons, or hydrogen;

and pharmaceutically acceptable acid-addition salts thereof.

The foregoing compounds possess central nervous system stimulating properties and act as muscle relaxants.

DETAILED DESCRIPTION

The final compound I of the present invention may be prepared by reacting a 2-aminopyrimidine II wherein R is as previously defined with an o-bromophenoxyalkylene halide III wherein R'' is as previously defined and X is chlorine or bromine. This reaction takes place in any solvent or solvent mixture in which the reactants can be dissolved and which has a boiling point of at least about 100°C. Typical solvents are aromatic hydrocarbons, ethers, aliphatic alcohols or arylsubstituted aliphatic alcohols. Toluene and xylene are examples of suitable aromatic hydrocarbons. Monomethyl ether of diethylene glycol, dimethyl ether of diethylene glycol (diglyme), monomethyl ether of ethylene glycol or dimethyl ether of ethylene glycol (glyme) are examples of suitable ethers. n-Amyl alcohol is an example of a suitable aliphatic alcohol, while benzyl alcohol is an example of a suitable arylsubstituted aliphatic alcohol. Heating compounds II and III in a solvent as described above, or a mixture thereof, at temperatures from about 100° to about 140°C for a period of several hours, typically from about 3 to about 24 hours produces pyrimidinium compound IV. The latter is converted to an imino compound V by treating with a water miscible alcohol and an alkali metal alkoxide of up to 3 carbon atoms or an alkali metal carbona. The reaction takes place at room temperature over a period of from about 1 to about 4 hours. Compound V may be converted to the final compound I by treating with a water miscible alcohol and an alkali metal alkoxide of up to 3 carbons in the presence of copper at a temperature of from about 60° to about 120° for about 4 to 10 days, typically from about 6 to about 8 days. Alternatively, IV may be converted directly to I by heating at a temperature of from about 60° to about 120°C for about 4 to 10 days, typically from about 6 to about 8 days in the presence of potassium carbonate and copper in a solvent such as dimethylformamide, dimethylacetamide, dichlorobenzene, trichlorobenzene, or diethylbenzene. Alternatively, however, IV may be converted directly to I by heating at a temperature of from about 60° to about 120°C for about 4 to 10 days, typically from about 6 to about 8 days in the presence of an alkali metal hydroxide, alkali metal carbonate, tris-alkali metal phosphate, alkali metal metaborate or alkali metal tetraborate in a solvent comprising a mixture of water and a water miscible alcohol in the presence of copper. Specific examples of suitable compounds include LiOH, NaOH, KOH, RbOH, CsOH, $Na_2CO_3$, $K_2CO_3$, $Rb_2CO_3$, $Cs_2CO_3$, $Na_3PO_4$, $K_3PO_4$, $Rb_3PO_4$, $Cs_3PO_4$, $Na_2B_2O_4$, $Na_2B_4O_7$, $K_2B_2O_4$, and $K_2B_4O_7$. The ratios of water and alcohol in the mixture of water and a water miscible alcohol are such that a homogeneous single phase system results.

When m is 1, and R occupies only the 5-position of II, only one isomer, I, is formed, When m is 1 and when R occupies only the 4-position of IIa, and R' occupies only the 5-position of III, two isomers, Ia and Ib are formed via the intermediates IVa or Va and IVb and Vb, respectively. When m is 2, and since the two R's occupy only the 4-, 5-positions, two isomeric products, Ic and Id are formed. The isomers, in all instances, can be separated by conventional procedures, e.g., fractional recrystallization or column chromatography.

The foregoing reaction sequences are illustrated by the following equations:

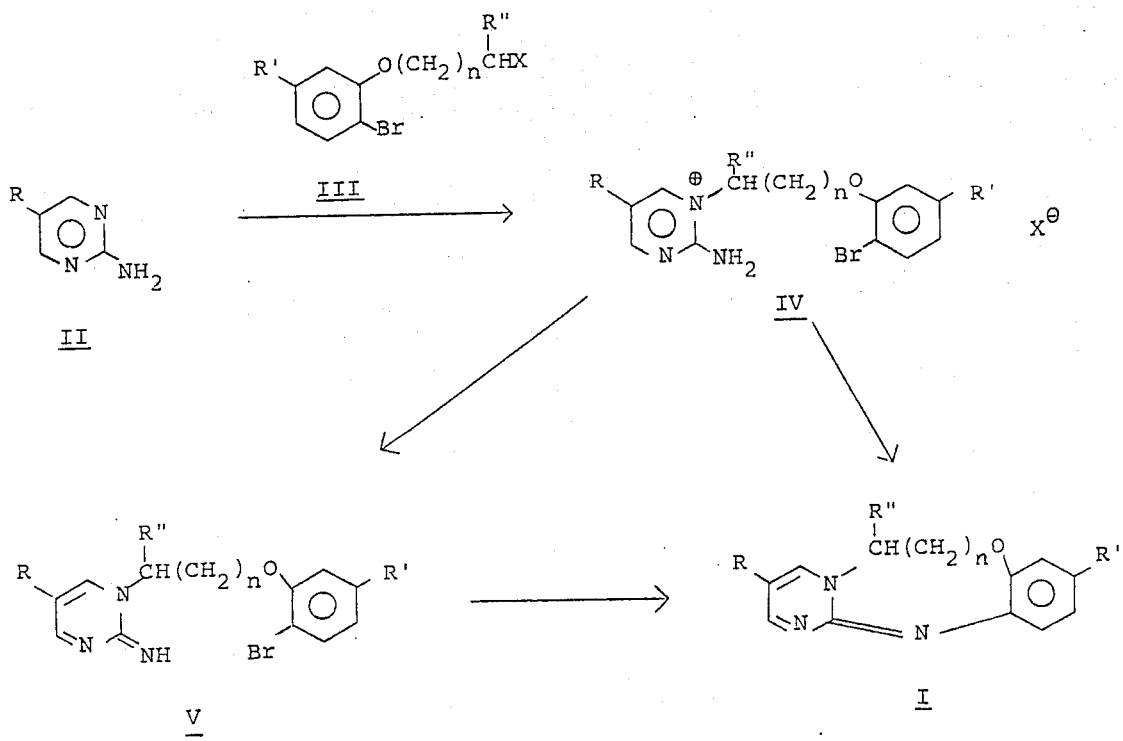
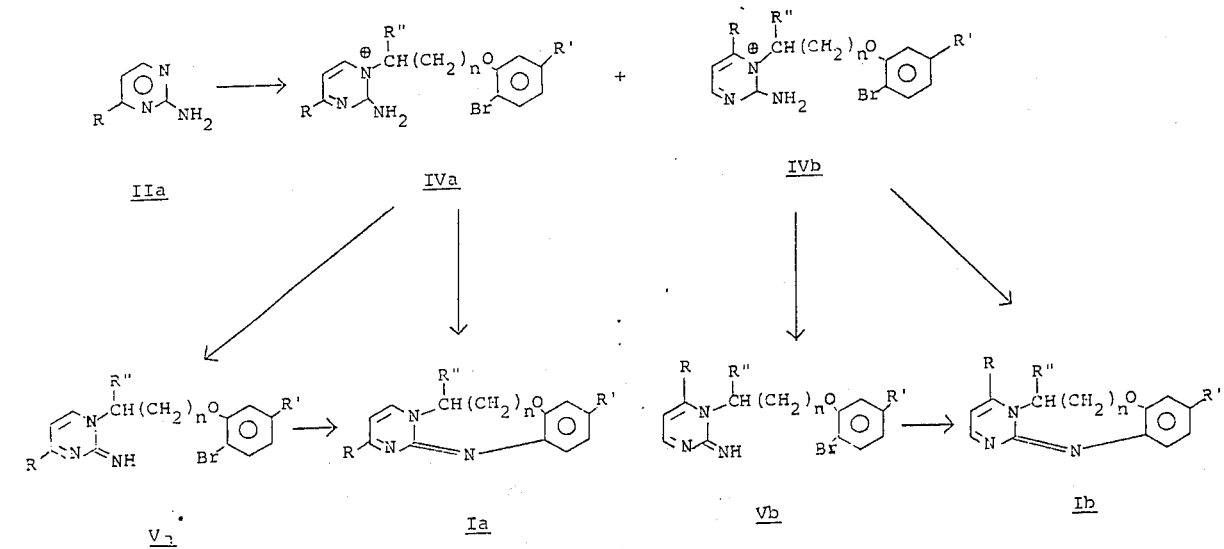

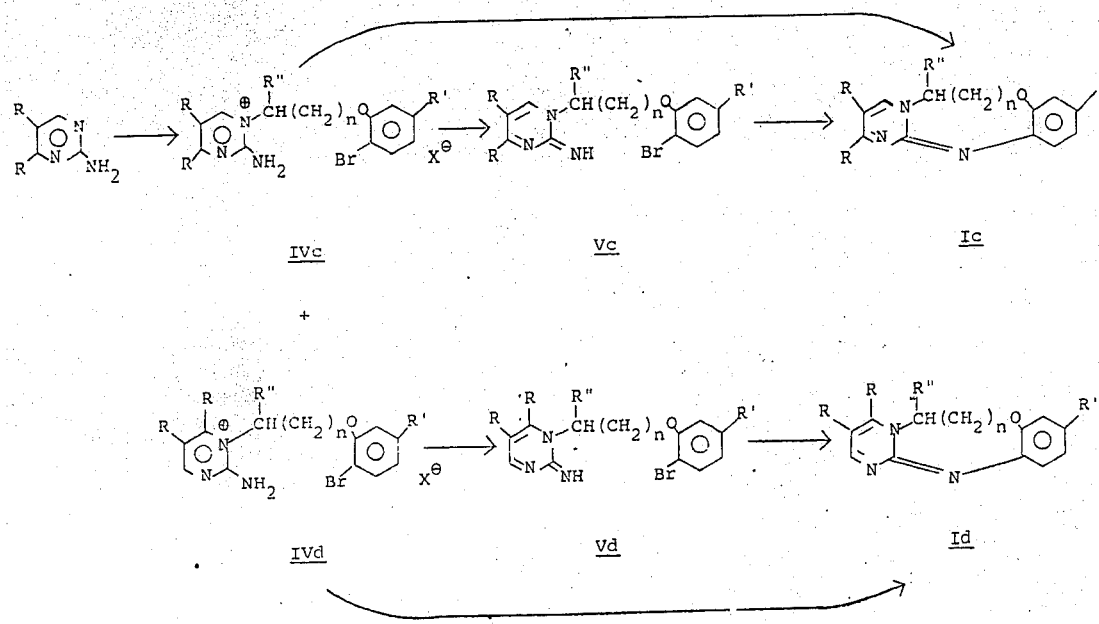

The intermediates of formula III wherein n is 0 may be prepared by refluxing about equimolar amounts of a 1,1-dibromoalkane or a 1-bromo-1-chloroalkane of 1 to 4 carbons VI with a saturated solution of Na$_2$SO$_3$ for a period of from about 40 to about 120 hours. The resulting 1-bromoalkane-1-sodium sulfonate VII is then reacted by heating with about equimolar amounts of an o-bromophenol VIII in the presence of aqueous alkali to yield a sodium o-bromophenoxyalkylenesulfonate IX. Treatment of the latter with PCl$_5$ or PBr$_5$ at ambient temperature yields the corresponding o-bromophenoxyalkyl chloride or bromide X. The foregoing reaction sequence is illustrated by the following equations

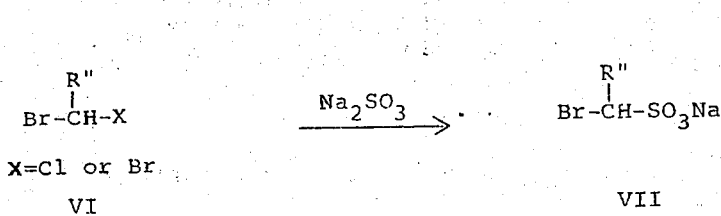

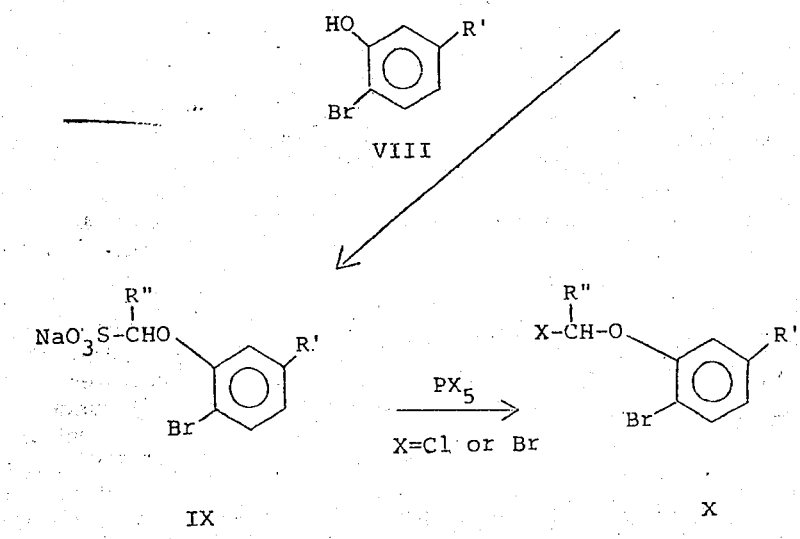

The intermediates of formula III wherein n is 1 may be prepared by reacting a 1-bromo-2-chloroalkane of formula XI with about equimolar amounts of a compound of formula VIII in the presence of aqueous alkali. Alternatively, a compound of formula XII may be prepared by reacting an o-bromophenoxyalkanol XIII with PCl$_5$ or PBr$_5$. The foregoing reaction sequence is illustrated by the following equations:

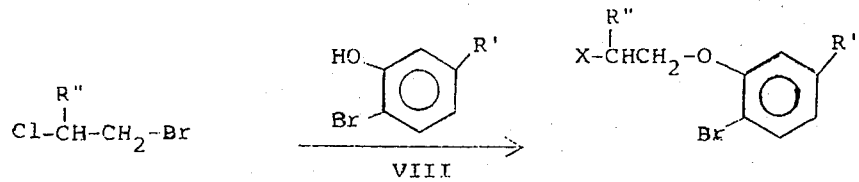

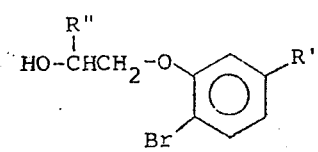

Compounds of Formula VIII wherein R' is fluorine, trifluoromethyl, alkylsulfonyl, or dialkylamidosulfonyl may be prepared by the following sequence of reactions

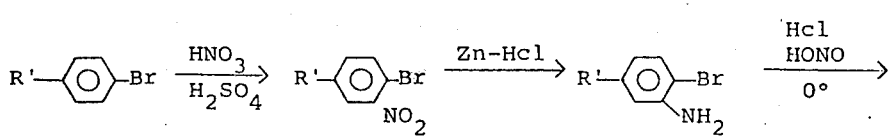

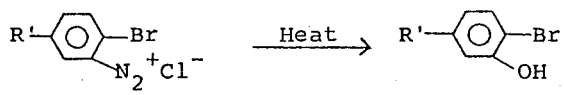

all of which are conventional and can be effected by procedures well-known in the art.

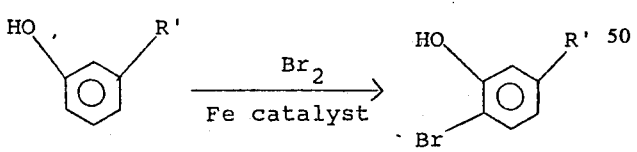

R' = —F, —CF$_3$ or —S—alkyl

The compounds of the present invention may be administered to mammalian species as central nervous system stimulants and as muscle relaxants. In the rat, responses to the stimulant activity of the compounds of the present invention include increased activity and body tremors. The muscle relaxant properties manifest themselves by responses that include decreased limb tone, decreased grip strength, and limb paralysis. In both the stimulant and muscle relaxant activities, the onset of activity is rapid, i.e., within about 15 minutes; the activity persists for about 2 hours or longer. In the rat the dosage range varies from about 6.25 to about 50 mg/kg for both activities, while in humans the dosage range varies from about 40 to about 2000 mg. daily in about four divided doses for both activities.

In addition to serving as intermediates for the preparation of compounds of formula I, the pyrimidinium compounds of formula IV are themselves effective bactericides.

Microbial bioassays, as described in "The Microbial World," by R. Y. Stanier, M. Doudoroff and E. A. Adelberg, Prentice-Hall, Inc., Englewood Cliffs, N.J., 3rd. Ed., p. 858, are employed to determine the bactericidal properties of the pyrimidinium compounds IV of this invention. The bacteria employed include Staphylococcus aureus, 1, Streptococcus pyogenes, 2, Salmonella schottmuelleri, 3, Salmonella gallinarum, 4, Pseudomonas aeruginosa, 5, Proteus vulgaris, 6, Escherichia coli, 7, Pasturella multocida, 8, and Mycobacterium tuberculosis, 9.

In the procedure, a sterile agar plate is seeded with the test organism, and then a number of glass cylinders are placed on its surface, forming a series of little cups. A known dilution of the compounds of this invention is added to each cup and the entire plate is then incubated until significant bacterial growth has occurred. The compounds of this invention diffuse out of the cup into the surrounding agar and produce a zone of inhibition. In this fashion it is possible to find the minimum inhibiting concentration (mic), of the compound that produces a recognizable zone of inhibition. The following summarizes the data.

| Micro-organism | mic of Pyrimidinium Compound, Micrograms, (mcg)/ml | | | |
|---|---|---|---|---|
| | Compound of Ex. 1 | Compound of Ex. 4 | Compound of Ex. 5 | Compound of Ex. 11 |
| 1 | 3.13 | 12.5 | 6.25 | 6.25 |
| 2 | 12.5 | 50.0 | 50.0 | 25.0 |
| 3 | 12.5 | 50.0 | 12.5 | 12.5 |
| 4 | 6.25 | 25.0 | 12.5 | 12.5 |
| 5 | 12.5 | 25.0 | 25.0 | 25.0 |
| 6 | 12.5 | 25.0 | 25.0 | 25.0 |
| 7 | 3.13 | 25.0 | 12.5 | 6.25 |
| 8 | 6.25 | 12.5 | 25.0 | 12.5 |
| 9 | 0.39 | 6.25 | 1.57 | 0.78 |

The compounds of the present invention in the described dosages may be administered orally; however, other routes such as intraperitoneally, subcutaneously, intramuscularly or intravenously may be employed.

The active compounds of the present invention are orally administered, for example, which an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added orr a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of the invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

The following examples illustrate the present invention without, however, limiting the same thereto. All temperatures in the following examples as well as the preceding description are expressed in degrees Centigrade.

EXAMPLE 1

6$\underline{H}$-Pyrimido[1,2-c] [1,3,5]benzoxadiazepine, hydrochloride

A. Sodium bromomethane sulfonate

A mixture of 372.0 g of dibromomethane and a saturated solution of 261.0 g of sodium sulfite in 750 ml of water is refluxed with stirring for about 80 hours. The reaction mixture is concentrated by distillation (600 ml of water is removed); the residue solidifies on standing. The solid, 608 g, is recrystallized from 200 ml of water to give about 380.0 g of the product, mp about 277°–281°.

B. (o-Bromophenoxy)methanesulfonic acid, sodium salt

To a solution of 61.3 g of o-bromophenol in aqueous NaOH solution [15.5 g of sodium hydroxide in 61 ml of water], is added 68.0 g of sodium bromomethanesulfonate. While stirring, the reaction mixture is slowly heated to 150°, in an oil bath, with simultaneous removal of water. In about 3 hours of heating, 61 ml of water is distilled, and the residue solidifies; this is further heated at 200° for about 2.5 hours. The solid is dissolved in 800 ml of warm water, the solution filtered and the filtrate adjusted to pH 5 and washed with 2 × 200 ml of ether. The aqueous phase is concentrated to 600 ml and cooled. The crystalline solid is filtered and dried in vacuo to give 63.3 g of the product, which is recrystallized from 600 ml of 90% aqueous ethanol to furnish about 57.5 g of the title product, mp about 282°–284°.

C. o-Bromo-α-chloroanisole

A mixture of 29.0 g of (o-bromophenoxy)methane sulfonic acid, sodium salt and 50.0 g of $PCl_5$ are thoroughly blended in a mortar. After about 10 minutes of continuous mixing, the mixture partly melts, a vigorous reaction occurs, and the whole turns to a liquid. The mixture is kept 15 minutes with occasional stirring, 700 ml of ether is added (a white solid separates) and the mixture is poured into 750 g of crushed ice. The ether solution is separated, washed, dried, and concentrated in vacuo to give about 21.0 g of a liquid residue. This is distilled under reduced pressure to give about 19.5 g of the colorless liquid product, $b_{2.0}$ 74°–75°, $n_D^{24.5}$ 1.5799.

D. 2-Amino-1-[(o-bromophenoxy)methyl]-pyrimidinium chloride

To a solution of 7.1 g of 2-aminopyrimidine in 35 ml of xylene is added, dropwise,, a solution of 11.1 g of o-bromo-α-chloroanisole in 45 ml of xylene. The mixture is warmed at 50° for 5 minutes and allowed to stir for 40 hours at room temperature. The solid is filtered and dried to give about 16.0 g of the product. This is recrystallized from 2-propanol to give about 14.0 g of the title product.

E. 6$\underline{H}$-Pyrimido[1,2-c] [1,3,5]benzoxadiazepine

A mixture of 9.5 g of 2-amino-1-[(o-bromophenoxy)-methyl]pyrimidinium chloride, 8.3 g of potassium carbonate, and 0.4 g of copper-bronze in 150 ml of n-propanol, under $N_2$, is heated under reflux for about 7 days while stirring. The mixture is filtered hot and the deep yellow filtrate is concentrated to dryness. The residue is dissolved in 400 ml of ether, the ether solution is washed, dried and the solvent removed to give about 6.4 g of the crude yellow product. This is recrystallized from cyclohexane to give about 3.6 g of the title product.

F. 6H-Pyrimido[1,2-c] [1,3,5]benzoxadiazepine, hydrochloride

To a solution of 1.0 g of 6H-pyrimido[1,2-c] [1,3,5]-benzoxadiazepine in 20 ml of 2-propanol is added 5.0 ml of 4.2N 2-propanolic hydrogen chloride. To the clear solution is added anhydrous ether until a turbidity forms. The pale yellow crystalline solid is filtered and recrystallized from acetonitrile to give about 1.0 g of the title compound.

EXAMPLE 2

6H-Pyrimido[1,2-c] [1,3,5]benzoxadiazepine

A. 1-(o-Bromophenoxymethyl)-1,2-dihydro-2-iminopyrimidine

A suspension of 7.0 g of the product from Example 1D, 5.6 g of micronized, anhydrous potassium carbonate, and 175 ml of anhydrous n-propanol is stirred and heated under reflux for about eight hours, filtered hot, and the filtrate concentrated to dryness in vacuo. The residue, about 6.3 g, is dissolved in 150 ml of ether, the ether solution is washed with water, saturated aqueous sodium chloride, dried and concentrated to give 1-(o-bromophenoxymethyl)-1,2-dihydro-2-iminopyrimidine. Recrystallization from pentane gives about 5.8 g of the pure product.

B. 6H-Pyrimido[1,2-c] [1,3,5]benzoxadiazepine

To a solution of 4.65 g of the product from A in 150 ml of n-propanol is added 0.20 g of copper bronze and 5.6 g of micronized, anhydrous, potassium carbonate, and the stirred suspension is heated under reflux for about ten hours. Workup as in Example 1E gives about 2.78 g of the title compound.

EXAMPLES 3 – 13

Following the procedure of example 1D, but substituting for 2-aminopyrimidine in part D the substituted pyrimidine listed below, there is obtained the correspondingly substituted compound of formulas IV, IVa, IVb, IVc or IVd wherein R' and R'' are hydrogen and n=0 which compound, following the procedure of Example 2, Part A, is then converted to the correspondingly substituted compound of formula V, Va, Vb, Vc and Vd which is then converted to the correspondingly substituted compound of formula I, Ia, Ib, Ic and Id, by following the procedure of Example 2, part B.

Example No.

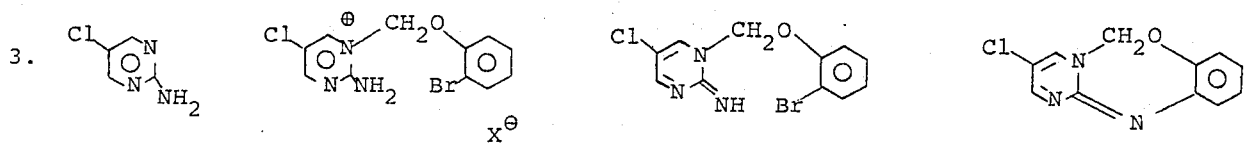

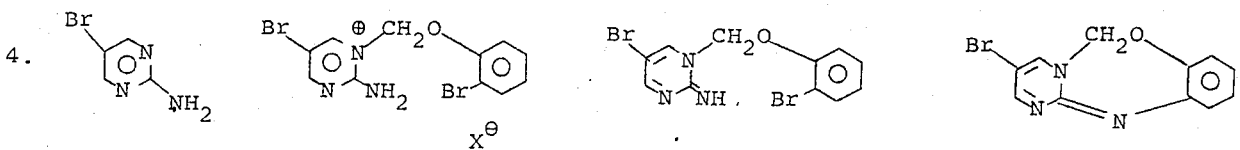

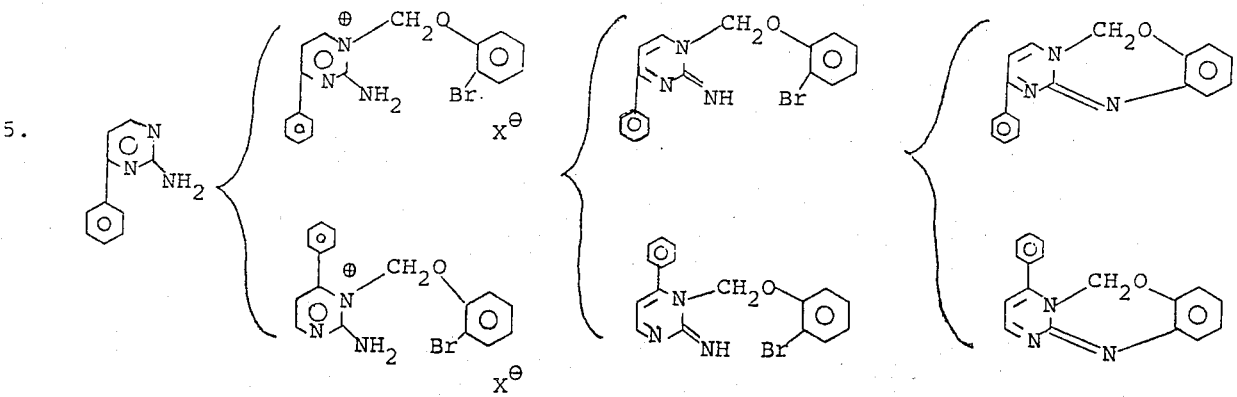

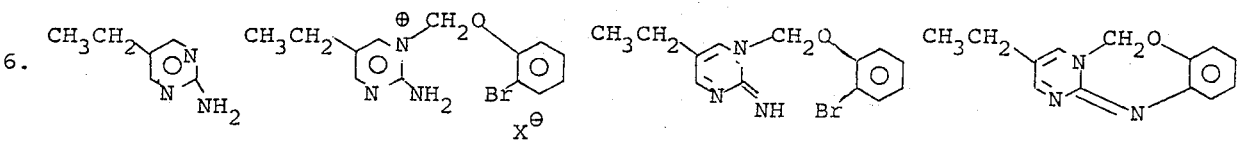

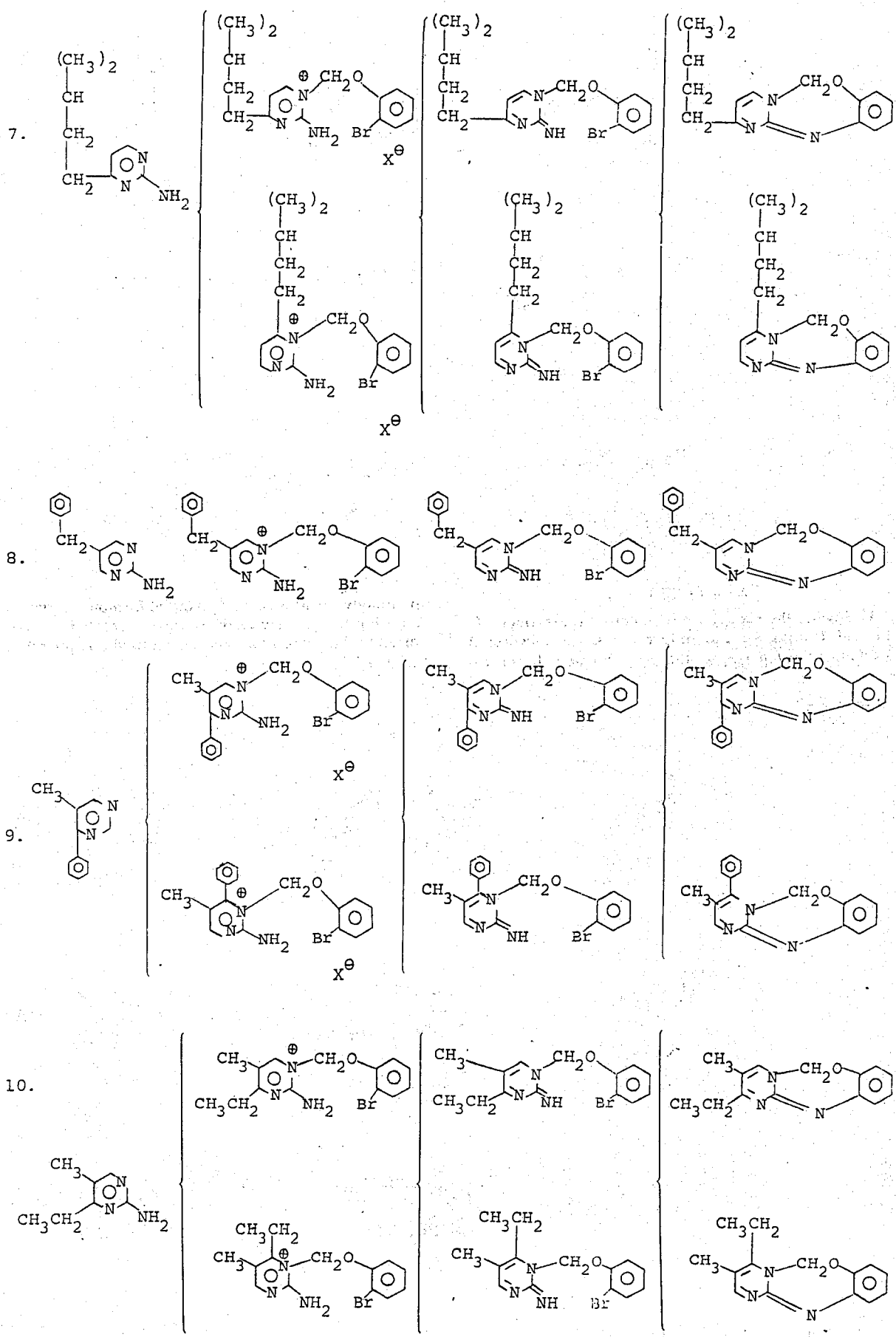

Example
No.
11.
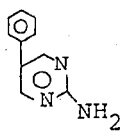 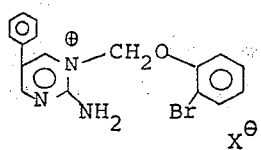 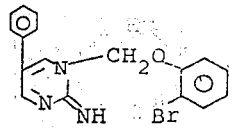 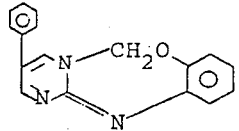
12.
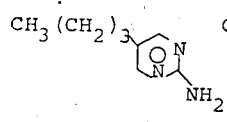 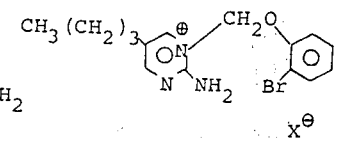 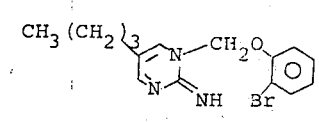 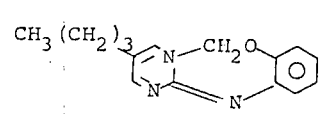
13.
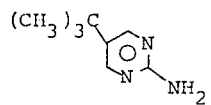 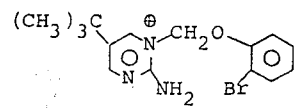 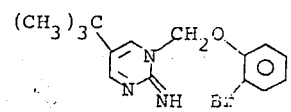 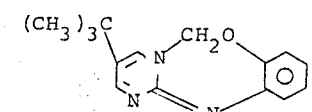
EXAMPLES 14 – 23
Following the procedure of example 1A through 1D but substituting for 2-aminopyrimidine the substituted pyrimidine listed below, there is obtained the correspondingly substituted compound of formula IV, which following the procedure of example 1, part E, is converted to the correspondingly substituted compound of formula I.
Example
No.
14.
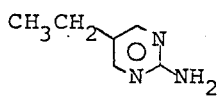 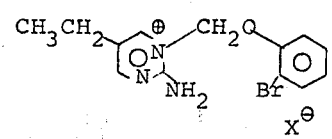 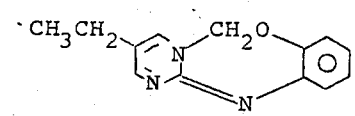
15.
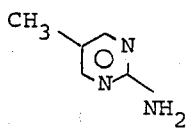 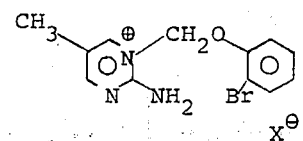 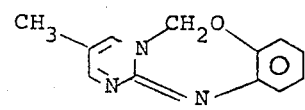
16.
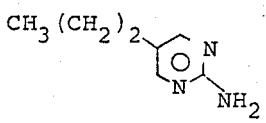 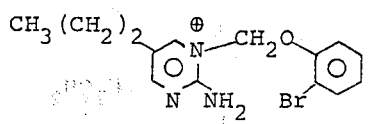 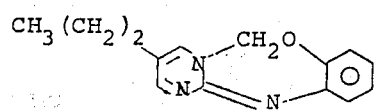

| Example No. | | | |
|---|---|---|---|
| 17. | 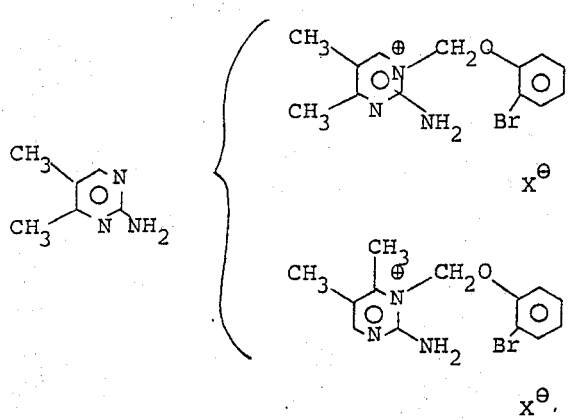 | | |
| 18. | 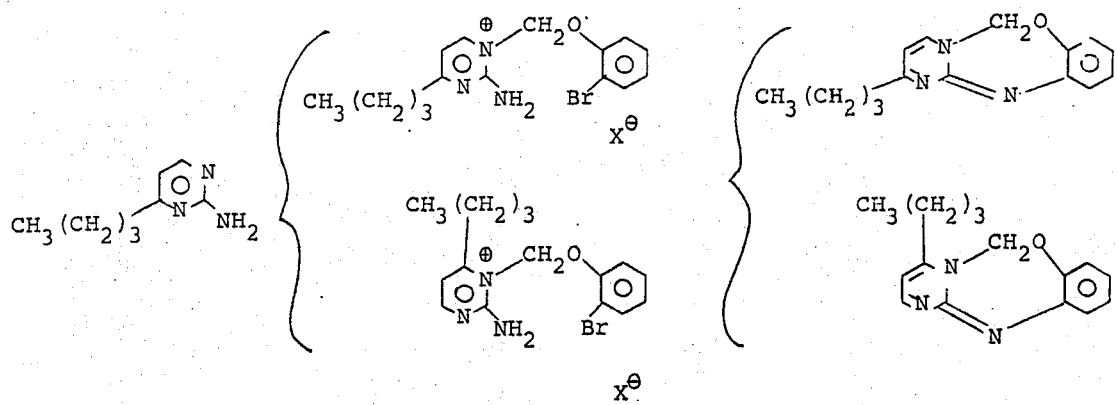 | | |
| 19. | 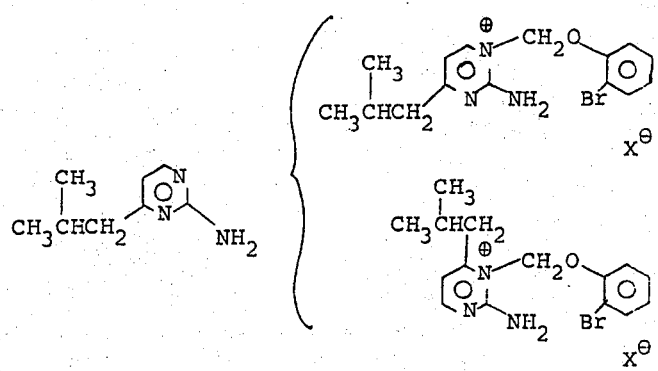 | | |
| 20. | 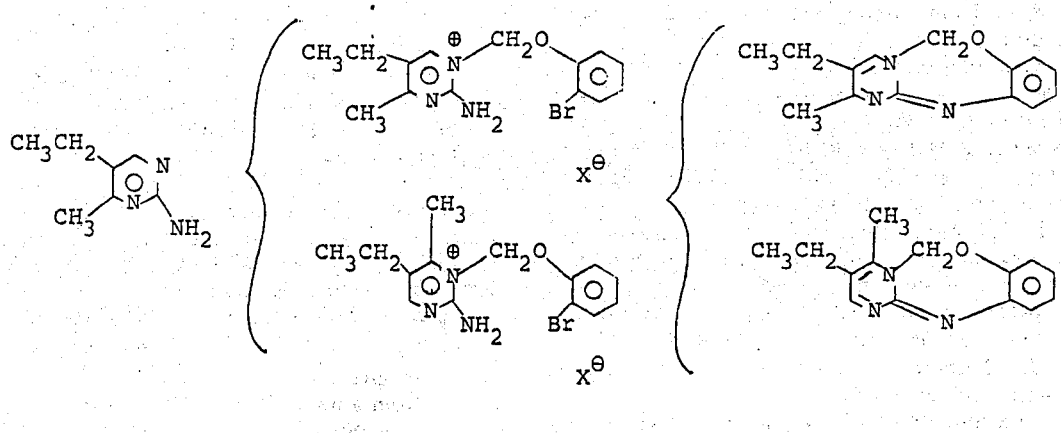 | | |

Example
No.

21.

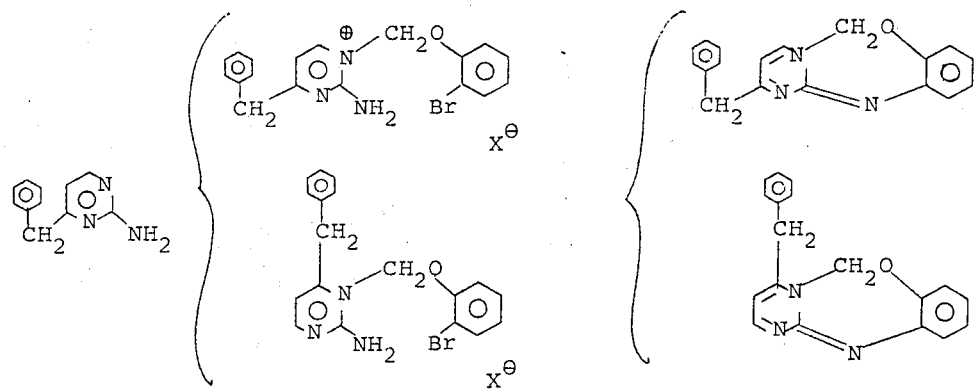

22.

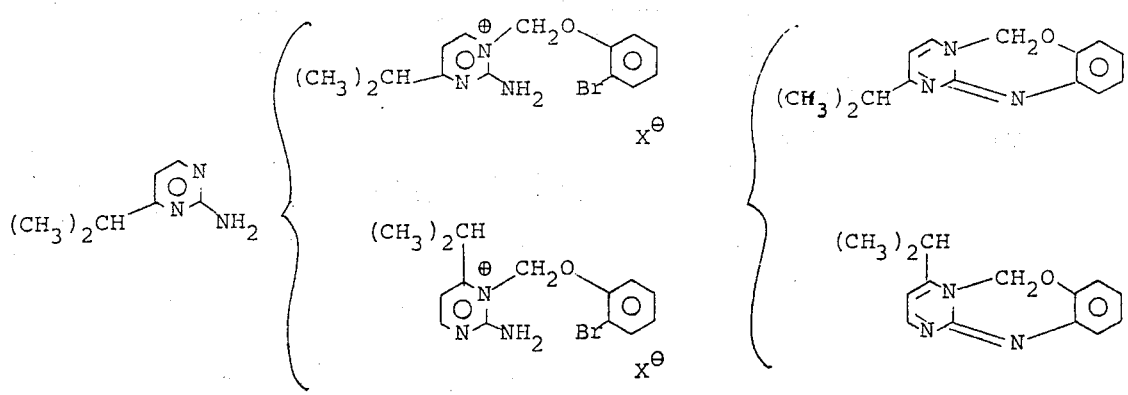

23.

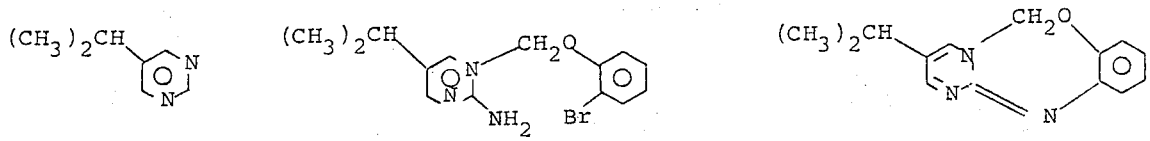

EXAMPLE 24

2-Chloro-6H-pyrimido[1,2-c][1,3,5]benzoxadiazepine hydrochloride

A. 2-Bromo-4-chlorophenoxymethanesulfonic acid, sodium salt

To a solution of 75.0 g of 2-bromo-4-chlorophenol in 65 ml of water is added 16.0 g of sodium hydroxide and 100g of bromomethanesulfonic acid, sodium salt. The procedure of Example 1, part B, is followed to give about 74.5 g of 2-bromo-4-chlorophenoxymethanesulfonic acid, sodium salt, m.p. above 315°.

B. 2-Bromo-4-chlorophenyl chloromethyl ether

A mixture of 71.0 g of the product from A and 110.0 g of phosphorus pentachloride is reacted as in Example 1, part C, to give about 55.7 g of 2-bromo-4-chlorophenyl chloromethyl ether, m.p. about 56.0° – 57.5°.

C. 2-Amino-1-[(2-bromo-4-chlorophenoxy)methyl]-pyrimidinium chloride

To a solution of 14.1 g of 2-aminopyrimidine in 180 ml of warm, anhydrous xylene is added 25.6 g of the product from B in 70 ml of anhydrous xylene and the mixture is stirred for about four hours at room temperature and then at 100° for about two hours to give about 33.0 g of 2-amino-1-[(2-bromo-4-chlorophenoxy)methyl]pyrimidinium chloride.

D. 2-Chloro-6H-pyrimido[1,2-c][1,3,5]benzoxadiazepine hydrochloride

A mixture of 14.0 g of 2-amino-1-[(2-bromo-4-chlorophenoxy)methyl]pyrimidinium chloride, 11.1 g of micronized, anhydrous potassium carbonate, 0.4 g of copper bronze, and 350 ml of anhydrous n-propanol is stirred and heated under reflux for about eight hours, filtered hot, and the deep yellow filtrate is concentrated to dryness in vacuo. Workup gives about 6.8 g of 2-chloro-6H-pyrimido[1,2-c][1,3,5]-benzoxadiazepine.

To the above base, 2.0 g in 50 ml of warm 2-propanol, is added about 5.0 ml of 4.8N 2-propanolic hydrogen chloride. The solid that separates is filtered to give about 2.2 g of product. This is recrystallized from a mixture of acetonitrile and absolute ethanol to give about 1.9 g of the title compound, m.p. about 303° – 305° (dec.).

EXAMPLES 25 – 40

Following the procedure of example 24 but substituting for 2-bromo-4-chlorophenol the substituted 2-bromophenol listed in column I, there is obtained the correspondingly substituted compound from parts B and C, and finally the compound of the following formula wherein R' and the position it occupies are indicated in column II.

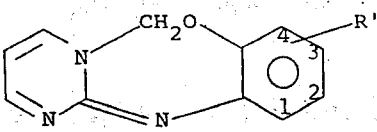

| Ex. | I | II |
|---|---|---|
| 25. | 2,5-dibromophenol | 3-bromo |
| 26. | 2-bromo-5-iodophenol | 3-iodo |
| 27. | 2-bromo-5-methylphenol | 3-methyl |
| 28. | 2-bromo-5-ethylphenol | 3-ethyl |
| 29. | 2-bromo-5-chlorophenol | 3-chloro |
| 30. | 2-bromo-5-n-butylphenol | 3-n-butyl |
| 31. | 2-bromo-5-isobutylphenol | 3-i-butyl |
| 32. | 2-bromo-5-fluorophenol | 3-fluoro |
| 33. | 6-bromo-α,α,α-trifluoro-m-cresol | 3-trifluoromethyl |
| 34. | 2-bromo-5-sulfamoylphenol | 3-sulfamoyl |
| 35. | 2-bromo-5-dimethylamidosulfonylphenol | 3-dimethylamidosulfonyl |
| 36. | 2-bromo-4-dibutylamidosulfonylphenol | 2-dibutylamidosulfonyl |
| 37. | 2-bromo-5-(methylsulfonyl)-phenol | 5-methylsulfonyl |
| 38. | 2-bromo-5-(n-butylsulfonyl)-phenol | 5-n-butylsulfonyl |
| 39. | 2-bromo-5-ethylsulfonylphenol | 2-ethylsulfonyl |
| 40. | 2-bromo-5-propylsulfonylphenol | 2-propylsulfonyl |

EXAMPLES 41 – 46

Following the procedure of example 1 but substituting for dibromoethane the compound listed in column I, there is obtained the compound of the following formula

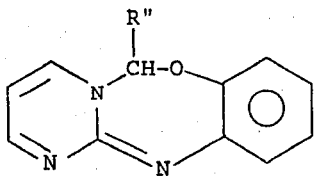

wherein R'' is as indicated in column II.

| Ex. | I | II |
|---|---|---|
| 41. | 1,1-dibromoethane | —CH₃ |
| 42. | 1,1-dibromoisobutane | CH(CH₃)₂ |
| 43. | 1,1-dibromopropane | —CH₂CH₃ |
| 44. | 1,1-dibromopentane | —(CH₂)₃CH₃ |
| 45. | 1,1-dibromobutane | —CH₂CH₂CH₃ |
| 46. | 1,1-dibromoisopentane | —CH₂CH(CH₃)CH₃ |

EXAMPLE 47

6,7-Dihydro-7-methyl-10-phenylpyrimido[1,2-d][1,4,6]-benzoxadiazocine

A. o-Bromophenyl 2-chloropropyl ether

To a solution of 23.0 g of sodium metal in 500 ml of absolute ethanol is added in about 0.5 hour a solution of 173.0 g of o-bromophenol in 250 ml of absolute ethanol. The mixture is stirred and heated under reflux for about 0.5 hours, cooled to 0°, and treated, dropwise, with 157.5 g of 1-bromo-2-chloropropane. The last addition requires about 1 hour. The mixture is stirred at 0° for about 2 hours and slowly warmed to reflux during about 2 hours, heated under reflux for about 2 hours, filtered from the precipitated sodium bromide, and the filtrate is concentrated in vacuo at 40° to give about 240.2 g of o-bromophenyl 2-chloropropyl ether as a mobile, colorless liquid.

B. 2-Amino-1-[2'-(o-bromophenoxy-1'-methylethyl)]-5-phenylpyrimidinium chloride

A solution of 29.4 g of 2-amino-5-phenylpyrimidine and 50.0 g of o-bromophenyl 2-chloropropyl ether and 200 ml of anhydrous toluene is heated under reflux for about 6 hours, cooled, and the crystalline product filtered to give about 60.2 g of 2-amino-1-[2'-(o-bromophenoxy-1'-methylethyl)]-5-phenylpyrimidinium chloride as a colorless, crystalline solid.

C. 1-[2'-(o-Bromophenoxy-1'-methylethyl)]-1,2-dihydro-2-imino-5-phenylpyrimidine To a solution of 8.5 g of the product from B in 100 ml of anhydrous n-propanol is added 2.8 g of anhydrous, micronized potassium carbonate and the mixture stirred and heated under reflux for about 1 hour. The hot suspension is filtered and the filtrate concentrated to give a pale yellow solid. This is recrystallized from cyclohexane to give about 5.8 g of 1-[2'-(o-bromophenoxy-1'-methylethyl)]-1,2-dihydro-2-imino-5-phenylpyrimidine as a pale yellow crystalline solid.

D. 6,7-Dihydro-7-methyl-10-phenylpyrimido-[1,2-d][1,4,6]benzoxadiazocine

The product from C, 3.39 g, 50 ml of anhydrous n-propanol, 2.8 g of anhydrous, micronized potassium carbonate, and 0.25 g of copper bronze are stirred and heated under reflux for about 6 hours, filtered hot, and the deep, yellow colored filtrate is concentrated to dryness in vacuo at 40°. The deep yellow-colored solid is recrystallized from ligroin to give about 2.22 g of 6,7 6,7-dihydro-7-methyl-10-phenylpyrimido[1,2-d][1,4,6]-benzoxadiazocine.

EXAMPLE 48

Preparation of capsule formulation

| Ingredient | Milligrams per Capsule |
|---|---|
| 6H-Pyrimido[1,2-c][1,3,5]benzoxadiazepine, hydrochloride | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 49

Preparation of tablet formulation

| Ingredient | Milligrams per Tablet |
|---|---|
| 2-Chloro-6H-pyrimido[1,2-c][1,3,5]benzoxadiazepine hydrochloride | 300 |
| Lactose | 200 |
| Corn starch (for mix) | 50 |
| Corn starch (for paste) | 50 |
| Magnesium stearate | 6 |

23

The active ingredient, lactose annd corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 50

Preparation of oral syrup formulation

| Ingredient | Amount |
| --- | --- |
| 6,7-Dihydro-7-methyl-10-phenylpyrimido-[1,2-d][1,4,6]benzodiazocine | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

24

What is claimed is:
1. A compound of the formula

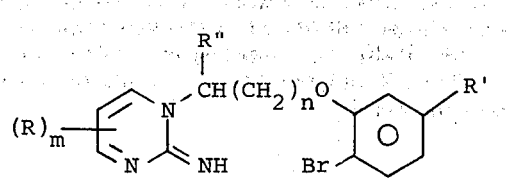

wherein $m$ is 1 or 2; when $m$ is 1, R occupies either position-4 or -5 of the starting 2-aminopyrimidine, but when R is halogen it occupies only position-5; when $m$ is 2, the two R's occupy the 4- and 5-positions of the starting 2-aminopyrimidine, but only one of the two R-substituents can be halogen and it must occupy the 5-position;

R is the same or different and is hydrogen, F, Cl, Br, alkyl of from 1 to 4 carbons, benzyl, phenyl, or minosubstituted phenyl wherein the substituent is F, Cl, Br, I, alkyl of from 1 to 4 carbons, alkoxy of from 1 to 4 carbons, or trifluoromethyl;

R' is hydrogen, F, Cl, Br, I, alkyl of from 1 to 4 carbons, alkylsulfonyl wherein the alkyl radical has from 1 to 4 carbons, dialkylamidosulfonyl wherein each alkyl radical has from 1 to 4 carbons, trifluoromethyl;

$n$ is 0 or 1;

and R" is hydrogen or alkyl of from 1 to 4 carbons.

2. A compound of claim 1 having the name 1-(o-bromophenoxymethyl)-1,2-dihydro-2-iminopyrimidine.

3. A compound of claim 1 having the name 1-[2'-(o-bromophenoxy-1'-methylethyl)]-1,2-dihydro-2-imino-5-phenylpyrimidine.

* * * * *

UNITED STATES PATENT AND TRADEMARK OFFICE
CERTIFICATE OF CORRECTION

PATENT NO. : 3,965,101
DATED : June 22, 1976
INVENTOR(S) : Harry Louis Yale et al.

It is certified that error appears in the above-identified patent and that said Letters Patent are hereby corrected as shown below:

On the title page, in the title, "O" should read --o--.
Column 1, line 1, "O" should read --o--.
Column 9, line 19, "which" should read --with--.
Column 9, line 38, "orr" should read --or--.
Column 21, after the first structure, delete the Roman numeral II
Column 22, line 40, delete "6,7".
Column 23, line 1, "annd" should read --and--.
Column 24, line 24, "minosubstituted" should read --monosubstituted--.

Signed and Sealed this

Twenty-first Day of September 1976

[SEAL]

Attest:

RUTH C. MASON
Attesting Officer

C. MARSHALL DANN
Commissioner of Patents and Trademarks